United States Patent [19]

Rentzea et al.

[11] Patent Number: 5,399,589
[45] Date of Patent: Mar. 21, 1995

[54] OXALYL HYDRAZIDE-HYDROXAMIC ACID DERIVATIVES, THEIR PREPARATION AND THEIR USE AS FUNGICIDES

[75] Inventors: Costin Rentzea, Heidelberg; Albrecht Harreus, Ludwigshafen; Eberhard Ammermann, Heppenheim; Gisela Lorenz, Neustadt, all of Germany

[73] Assignee: BASF Aktiengesellschaft, Ludwigshafen, Germany

[21] Appl. No.: 158,392

[22] Filed: Nov. 29, 1993

[30] Foreign Application Priority Data

Dec. 17, 1992 [DE] Germany .............. 42 42 751.7

[51] Int. Cl.$^6$ .............. A01N 37/18; C07C 243/24
[52] U.S. Cl. .............. 514/615; 514/315; 514/357; 514/358; 514/378; 514/432; 514/451; 514/461; 514/614; 546/247; 546/335; 548/240; 549/28; 549/424; 549/425; 564/148; 564/149; 564/151
[58] Field of Search ............ 514/614, 507, 575, 615; 560/312; 564/148, 151, 150, 149

[56] References Cited

FOREIGN PATENT DOCUMENTS

| | | | |
|---|---|---|---|
| 0232075 | 8/1987 | European Pat. Off. .......... | 514/614 |
| 0465986 | 1/1992 | European Pat. Off. . | |
| 0469423 | 2/1992 | European Pat. Off. .......... | 560/312 |
| 4022265 | 1/1992 | Germany . | |
| 44-27997 | 11/1969 | Japan ............................ | 514/614 |

OTHER PUBLICATIONS

Chemical Abstracts, vol. 89, No. 13, Sep. 25, 1978, AN 108560j, G. P. Petyunin, et al., "Amides and Hydrazides of Oxalic Acid. XXXVII. Synthesis and Biological Activity of Substituted Carbamidohydroxamic Acids".

*Primary Examiner*—Shailendra Kumar
*Attorney, Agent, or Firm*—Oblon, Spivak, McClelland, Maier & Neustadt

[57] ABSTRACT

Oxalyl hydrazide-hydroxamic acid derivatives of the formula I

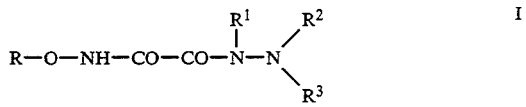

where the substituents have the following meanings:

R, $R^1$, $R^2$ and $R^3$ independently of one another are hydrogen, substituted or unsubstituted alkyl, alkenyl or alkynyl or substituted or unsubstituted cycloalkyl or cycloalkylmethyl, substituted or unsubstituted cycloalkenyl or cycloalkenylmethyl, substituted or unsubstituted phenyl, phenylalkyl, phenylalkenyl, hetaryl- or hetarylalkyl radicals, where $R^2$ and $R^3$ may also together with the nitrogen atom whose substituents they are, form a 5- or 6-membered ring, or $R^2$ together with $R^3$ is the group

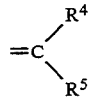

where $R^4$ and $R^5$ are one of the radicals R, $R^1$, $R^2$ or $R^3$, or $R^4$ together with $R^5$ and the carbon atom whose substituents they are, are monocyclic or polycyclic cycloalkyl, or $R^4$ together with $R^5$ and the carbon atom whose substituents they are, form a 5- or 6-membered, saturated heterocycle containing O, S or —N($R^6$)— as a hetero group, and fungicides containing these active ingredients.

13 Claims, No Drawings

OXALYL HYDRAZIDE-HYDROXAMIC ACID DERIVATIVES, THEIR PREPARATION AND THEIR USE AS FUNGICIDES

The present invention relates to novel oxalyl hydrazide-hydroxamic acid derivatives of the general formula I

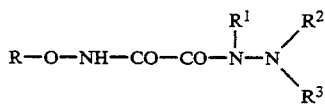

where the substituents have the following meanings:
R, $R^1$, $R^2$, and $R^3$ independently of one another are hydrogen, $C_1$–$C_{20}$-alkyl, $C_3$–$C_{18}$-alkenyl or $C_3$–$C_8$-alkynyl, where these radicals can carry one to five halogen atoms or one to three $C_1$–$C_4$-alkoxy groups, if appropriate together with the halogen atoms;
monocyclic or polycyclic $C_3$–$C_{10}$-cycloalkyl or $C_3$–$C_{10}$-cycloalkylmethyl, where these rings can carry one to three $C_1$–$C_4$-alkyl groups or a cyclohexyl ring;
monocyclic or polycyclic $C_5$–$C_{10}$-cycloalkenyl or $C_5$–$C_{10}$-cycloalkenylmethyl, where these rings can carry one to three $C_1$–$C_4$-alkyl groups or a cyclohexyl ring;
phenyl, phenyl-$C_1$–$C_4$-alkyl, phenyl-$C_2$–$C_6$-alkenyl, mononuclear heteroaryl or heteroaryl-$C_1$–$C_4$-alkyl radicals, where the (hetero)aromatic radicals can carry one to five halogen atoms or one to three of the following groups, if appropriate together with the halogen atoms: hydroxyl, nitro, $C_1$–$C_4$-alkyl, $C_1$–$C_4$-haloalkyl, $C_1$–$C_4$-alkoxy, $C_1$–$C_4$-haloalkoxy, COOR, $CONH_2$ or amines, where $R^2$ and $R^3$ can also form, together with the nitrogen atom whose substituents they are, a 5- or 6-member ring which additionally can be interrupted by oxygen, or
$R^2$ together with $R^3$ is the group

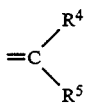

where $R^4$ and $R^5$ are one of the radicals R, $R^1$, $R^2$ or $R^3$ or $R^4$, together with $R^5$ and the C atom whose substituents they are, are monocyclic or polycyclic $C_3$–$C_{10}$-cycloalkyl, where these rings can carry one to three $C_1$–$C_4$-alkyl groups or a phenyl ring, or
$R^4$, together with $R^5$ and the C atom whose substituents they are, form a 5- or 6-membered, saturated heterocycle containing O, S or —$N(R^6)$— as a hetero group, where $R^6$ is a $C_1$–$C_6$-alkyl group, or with two non-adjacent identical or different heteroatoms, which can be oxygen, sulfur or the group —$N(R^6)$, as a hetero group, and compositions which contain these oxalyl hydrazidehydroxamic acid derivatives as active compounds, processes for their preparation and processes for the control of fungal attack on useful plants using these compounds.

It is an object of the present invention to provide novel compounds which have a high fungicidal activity and a good plant tolerability.

We have found that this object is achieved by the oxalyl hydrazide-hydroxamic acid derivatives I defined at the beginning and processes for their preparation.

According to the invention, compositions which contain these oxalyl derivatives as active compound and a process for the control of phytopathogenic fungi in useful plant crops using these compounds are provided.

Specifically, the radicals $R^1$ to $R^5$ in formula I have the following meanings:

R, $R^1$, $R^2$ and $R^3$ are identical or different and can be widely varied.

For example, they are hydrogen, straight-chain or branched $C_1$- to $C_{20}$-alkyl, in particular $C_1$- to $C_{16}$-alkyl such as methyl, ethyl, n-propyl, iso-propyl, n-butyl, iso-butyl, sec-butyl, pentyl, hexyl, heptyl, octyl, nonyl, decyl, undecyl, tridecyl, tetradecyl, pentadecyl, hexadecyl, heptadecyl, octadecyl and nonadecyl; straight-chain or branched $C_1$–$C_{20}$-haloalkyl, in particular $C_1$–$C_{12}$-haloalkyl having 1 to 5, for example 1 to 3, preferably 1 to 2 halogen atoms, such as iodine, bromine, in particular fluorine or chlorine, such as chlorobutyl, e.g. 1-chlorobutyl, 2-chlorobutyl, 3-chlorobutyl, 4-chlorobutyl, 2,3-dichlorobutyl, chlorohexyl, e.g. 3-chlorohexyl, 5-chlorohexyl, fluoropentyl, e.g. 3-fluoropentyl, fluorohexyl, fluoroheptyl, fluorodecyl, fluorododecyl; $C_3$–$C_{18}$-alkenyl, in particular $C_3$–$C_{16}$-alkenyl having 1 to 3 double bonds in the alkenyl radical, such as allyl, methallyl, pentenyl, hexenyl, heptenyl, octenyl, 2-chloroallyl, 2-bromoallyl, 3-chloroallyl, 3-bromoallyl, 2,3,3,-trichloroallyl, 3-chloro-2-butenyl, decenyl, dodecenyl, geranyl, hexadecenyl, octadecenyl; $C_3$- or $C_4$-alkynyl, such as propargyl or 2-butinyl; unbridged or bridged, i.e. bearing 1 or 2 methylene or ethylene bridges, $C_3$–$C_{10}$-cycloalkyl or $C_3$–$C_{10}$-cycloalkylmethyl, in particular $C_3$–$C_8$-cycloalkyl or $C_3$–$C_8$-cycloalkylmethyl, it being possible for said cycloalkyl or cycloalkylalkyl radicals to be $C_1$–$C_5$-alkyl-substituted or cyclohexyl-substituted. For example, the following radicals may be mentioned, cycloalkyl radicals such as cyclopropyl, cyclopentyl, methylcyclopentyl, cyclohexyl, ethylcyclohexyl, propyl- and isopropyl-cyclohexyl, butyl-, iso-butyl-, sec-butyl- and tert-butyl-cyclohexyl, tert-amylcyclohexyl, cyclohexylcyclohexyl, cycloheptyl, methylcycloheptyl, propylcycloheptyl, cyclooctyl, cyclododecyl, decalyl (decahydronaphthyl); cycloalkylmethyl radicals, such as cyclopropylmethyl, cyclopentylmethyl, cyclohexylmethyl, cyclododecylmethyl; bridged cycloalkyl or cycloalkyl-methyl radicals such as norbornyl, 1,5-dimethylbicyclo[2.3.1]octan-8-yl, tricyclodecanyl, norbornylmethyl, adamantyl and mono- and bicyclic terpene radicals such as o-menthyl, m-menthyl, p-menthyl, bornyl, isobornyl, pinanyl, camphenyl and homocamphenyl.

The radicals R, $R^1$, $R^2$ and $R^3$ are furthermore phenyl, phenyl-$C_1$–$C_4$-alkyl, phenyl-$C_2$–$C_6$-alkenyl, mononuclear heteroaryl or heteroaryl-$C_1$–$C_4$-alkyl radicals, which can be substituted by halogen, hydroxyl, nitro, $C_1$–$C_4$-alkyl, $C_1$–$C_4$-haloalkyl, $C_1$–$C_4$-alkoxy, $C_1$–$C_4$-haloalkoxy, COOR, $CONH_2$ or amino groups, in particular phenyl, phenylmethyl, phenylethyl, phenylpropyl, 2-fluorophenyl, 3-fluorophenyl, 4-fluorophenyl, 2-chlorophenyl, 3-chlorophenyl, 4-chlorophenyl, 4-bromophenyl, 2,3-dichlorophenyl, 2,4-dichlorophenyl, 3,4-dichlorophenyl, 2-hydroxyphenyl, 3-hydroxyphenyl, 4-hydroxyphenyl, 2-hydroxy-3-chlorophenyl, 2,6-dichlorophenyl, 2-hydroxy-5-chlorophenyl, 2-hydroxy-2,5-dichlorophenyl, 2-hydroxy-3-bromophenyl, 2-hydroxy-2,5-dibromophenyl, 4-hydroxy-3,5-dichlorophenyl, 4-hydroxy-3,5-dibromophenyl, 2-hydroxy-3-methoxyphenyl, 2-hydroxy-4-methoxyphenyl, 2-hydroxy-5-methoxyphenyl, 3-methoxy-4-hydroxyphenyl, 4-hydroxy-3-methoxyphenyl, 2-methylphenyl, 3-methylphenyl, 4-methylphenyl, 2,4-dimethylphenyl, 2,5-dimethylphenyl, 2,6-dimethylphenyl, 4-iso-propylphenyl, 4-tert-butylphenyl, 4-sec-butylphenyl, 2-trifluoromethylphenyl, 3-trifluoromethylphenyl, 4-trifluoromethylphenyl, 4-nitrophenyl, 2-hydroxy-3-nitrophenyl, 2-hydroxy-5-nitrophenyl, 2-methoxyphenyl, 3-methoxyphenyl, 4-methoxyphenyl, 4-ethoxyphenyl, 4-butoxyphenyl, 2,3-dimethoxyphenyl, 2,4-dimethoxyphenyl, 2,5-dimethoxyphenyl, 3,4-dimethoxyphenyl, 3,5-dimethoxyphenyl, 2,3,4-trimethoxyphenyl, 3,4,5-trimethoxyphenyl, 2-fluorobenzyl, 3-fluorobenzyl, 4-fluorobenzyl, 2-chlorobenzyl, 3-chlorobenzyl, 4-chlorobenzyl, 4-bromobenzyl, 2,4-dichlorobenzyl, 2,6-dichlorobenzyl, 3,4-dichlorobenzyl, 4-nitrobenzyl, 2-methylbenzyl, 3-methylbenzyl, 4-methylbenzyl, 2,4-dimethylbenzyl, 3,4-dimethylbenzyl, 2,5-dimethylbenzyl, 4-iso-propylbenzyl, 4-sec-butylbenzyl, 4-tert-butylbenzyl, 4-methoxybenzyl, 4-carboxyethylbenzyl, 2-trifluoromethylbenzyl, 3-trifluoromethylbenzyl, 4-trifluoromethylbenzyl, 2-thienyl, 3-thienyl, 2-furanyl, 3-furanyl, 3-isoxazolyl, 4-isoxazolyl, 5-isoxazolyl, 2-thiazolyl, 2-thienylmethyl, 5-chloro-2-thienyl, 5-chloro-2-thienylmethyl, 5-bromo-2-thienyl, 5-chloro-3-thienyl, 5-bromo-3-thienyl, 5-methyl-2-thienyl, 5-methyl-2-thienylmethyl, 2-furanylmethyl, 5-methyl-2-furanyl, 5-methyl-2-furanylmethyl, 5-nitro-2-furanyl, 5-nitro-2-thienyl, 3-isoxazolylmethyl, 4-isoxazolylmethyl, 5-isoxazolylmethyl, 2-pyridinyl, 3-pyridinyl, 4-pyridinyl, 2-pyridinylmethyl, 3-pyridinylmethyl, 4-pyridinylmethyl.

Furthermore, $R^4$, together with $R^5$ and the C atom whose substituents they are, are also N-methyl-piperidinylene, N-methylpyrrolidinylene, tetrahydropyranylidene, tetrahydrofuranylidene, hexahydrooxazinylidene, hexahydrothiazinylidene or dithianylidene radicals.

The novel compounds can be prepared by reacting
a) hydrazines of the formula II

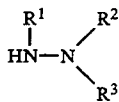
(II)

with an oxalylhydroxamic ester of the formula III

where R, , $R^1$, $R^2$, $R^3$ and $R^6$ have the abovementioned meanings, or
b) an oxalyl hydrazide-hydroxamic acid ester of the formula IV

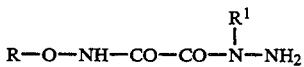
(IV)

with an aldehyde or ketone of the formula V

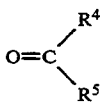
(V)

where R, $R^1$, $R^4$ and $R^5$ have the abovementioned meanings, if appropriate in the presence of a solvent or diluent or an inorganic or organic base or an inorganic or organic acid or a reaction accelerator or mixtures thereof.

Useful solvents for process variant a) are, for example, halohydrocarbons, in particular chlorohydrocarbons, e.g. 1,1,2,2-tetrachloroethylene, or 1,1,2,2-tetrachloroethane, dichloropropane, methylene chloride, dichlorobutane, 1,1,1- or 1,1,2-trichloroethane, trichloroethylene, o-, m-, or p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o-, p- or m-dibromobenzene, o-, m-, or p-chlorotoluene; ethers, e.g. ethyl propyl ether, methyl tert-butyl ether, n-butyl ethyl ether, di-n-butyl ether diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole; alcohols such as methanol, ethanol, propanol, isopropanol, n-butanol, isobutanol, tert-butanol, ethylene glycol and propanediols; nitriles such as acetonitrile, butyronitrile, isobutyronitrile, benzonitrile, m-chlorobenzonitrile; aliphatic or cycloaliphatic hydrocarbons, e.g. heptane, pinane, nonane, o-, m- or p-cymene, gasoline fractions within a boiling range from 70° to 190° C., cyclohexane, methylcyclohexane, decalin, petroleum ether, hexane, ligroin, 2,2,4-trimethylpentane, 2,2,3-trimethylpentane, 2,3,3-trimethylpentane, octane; esters e.g. ethyl acetate, acetoacetic ester, isobutyl acetate; amides, e.g. formamide, methylformamide, dimethylformamide, and, if appropriate, also water and appropriate mixtures. The compounds of the formula I can also be used in excess as solvents. Expediently, the solvent is used in an amount from 100 to 2000% by weight, preferably from 200 to 700% by weight, based on starting substance III.

Suitable bases are, for example, potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec-butylamine, tri-tert-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-4-aminopyridine, N,N-di-ethyl-4-aminopyridine, N,N-di-propyl-4-aminopyridine, N,N-dipropyl-4-aminopyridine, N-methylpyrolidine, N-ethylpyrrolidine, N-methylpiperidine, N-ethylpiperidine, N-methyl-pyrrolidine, N-ethyl-pyrrolidine, N-methylimidazole, N-ethylimidazole, N-methylmorpholine, N-ethylmorpholine, N-methylhexamethylenimine, N-ethylhexamethylenimine, pyridine, quinoline, alpha-picoline, beta-picoline, isoquinoline, pyrimidine, acridine, N,N,N', N'-tetramethylethylenediamine, N,N,N',N'-tetraethylethylenediamine, quinoxaline, N-propyldiisopropylamine, N,N-dimethylcyclohexylamine, 2,6-lutidine, 2,4-lutidine and triethylenediamine.

Expediently, the base is used in stoichiometric amounts, in an excess or a deficit of in each case up to 20 mol %, based on the starting substance III.

It may additionally be useful to carry out the reaction in the presence of a catalyst.

Suitable reaction accelerators are preferably 4-dimethylaminopyridine and 4-pyrrolidinopyridine (J. Cossy et al., Synthesis, (1989) 753f).

Starting substances of the formula III are disclosed in DE 4 022 265.

For process variant b), the reaction in general takes place at temperatures from −20° to 100° C., preferably from 15° to 80° C.

Useful solvents are, for example, those mentioned above in process a). The following are particularly suitable: acetic acid, ethyl acetate, methylene chloride, toluene, chlorobenzene, tetrahydrofuran, dioxane, methanol, ethanol, n-propanol, iso-propanol, n-butanol, iso-butanol and tert-butanol or mixtures thereof.

Suitable bases in this process in addition to the abovementioned are potassium acetate and sodium acetate.

Apart from the compounds mentioned in the preparation examples, the following oxalylhydrazide-hydroxamic acid derivatives of the general formula I may specifically be mentioned:

TABLE 1

| R | $R^1$ | $R^2$ | $R^3$ |
|---|---|---|---|
| H | H | H | H |
| $CH_3$ | H | H | H |
| $CH_3$ | $CH_3$ | H | H |
| $CH_3$ | $CH_3$ | $CH_3$ | H |
| $CH_3$ | H | $CH_3$ | $CH_3$ |
| $CH_3$ | $C_2H_5$ | H | H |
| $CH_3$ | n-$C_3H_7$ | H | H |
| $CH_3$ | iso-$C_3H_7$ | H | H |
| $CH_3$ | H | —C($CH_3$) | H |
| $CH_3$ | n-$C_4H_9$ | H | H |
| $CH_3$ | iso-$C_4H_9$ | H | H |
| $CH_3$ | n-$C_5H_{11}$ | H | H |
| $CH_3$ | iso-$C_5H_{11}$ | H | H |
| $CH_3$ | n-$C_6H_{13}$ | H | H |
| $CH_3$ | n-$C_8H_{17}$ | H | H |
| $CH_3$ | n-$C_{10}H_{21}$ | H | H |
| $CH_3$ | cyclopropyl | H | H |
| $CH_3$ | cyclopentyl | H | H |
| $CH_3$ | cyclohexyl | H | H |
| $CH_3$ | 4-methylcyclohexyl | H | H |
| $CH_3$ | cyclohexylmethyl | H | H |
| $CH_3$ | cycloheptyl | H | H |
| $CH_3$ | —$CH_2CH_2$—Cl | H | H |
| $CH_3$ | —$CH_2CH_2CH_2Cl$ | H | H |
| $CH_3$ | —$(CH_2)_4Cl$ | H | H |
| $CH_3$ | —$(CH_2)_5Cl$ | H | H |
| $CH_3$ | —$CH_2$—$CF_3$ | H | H |
| $CH_3$ | —$(CH_2)_5Br$ | H | H |
| $CH_3$ | —$CH_2$—$CH_2OCH_3$ | H | H |
| $CH_3$ | —$(CH_2)_3OCH_3$ | H | H |
| $CH_3$ | —$(CH_2)_2OC_2H_5$ | H | H |
| $CH_3$ | —$(CH_2)_3OC_2H_5$ | H | H |
| $CH_3$ | —$(CH_2)_4OCH_3$ | H | H |
| $CH_3$ | —$CH_2CH=CH_2$ | H | H |
| $CH_3$ | —$CH_2$—CH=CH—$CH_3$ | H | H |
| $CH_3$ | —$CH_2$—CH=CH($CH_3$)$_2$ | H | H |
| $CH_3$ | —$CH_2$CH=CH—$C_2H_5$ | H | H |
| $CH_3$ | —$CH_2$CH=CH—$C_3H_7$ | H | H |
| $CH_3$ | —$CH_2$C(Cl)=$CH_2$ | H | H |
| $CH_3$ | —$CH_2$C(Br)=$CH_2$ | H | H |
| $CH_3$ | —$CH_2$CH=CHCl | H | H |
| $CH_3$ | —$CH_2$CH=CHBr | H | H |
| $CH_3$ | H | —$C_6H_5$ | H |
| $CH_3$ | H | —$C_6H_5$ | $CH_3$ |
| $CH_3$ | H | —$C_6H_4$-4F | H |
| $CH_3$ | H | —$C_6H_4$-4Cl | H |
| $CH_3$ | H | —$C_6H_4$-2Cl | H |
| $CH_3$ | H | —$C_6H_4$-4Br | H |
| $CH_3$ | H | —$C_6H_4$-2$CH_3$ | H |
| $CH_3$ | H | —$C_6H_4$-3$CH_3$ | H |
| $CH_3$ | H | —$C_6H_4$-4$CH_3$ | H |
| $CH_3$ | H | —$C_6H_4$-4$CF_3$ | H |
| $CH_3$ | H | —$C_6H_4$-4$NO_2$ | H |
| $CH_3$ | H | —$C_6H_4$-4$OCH_3$ | H |
| $CH_3$ | H | —$C_6H_4$-4C($CH_3$)$_3$ | H |
| $CH_3$ | H | —$C_6H_4$-4($OC_2H_5$) | H |
| $CH_3$ | H | —$C_6H_4$-4-N($CH_3$)$_2$ | H |
| $CH_3$ | H | —$C_6H_4$-4-$CONH_2$ | H |
| $CH_3$ | H | —$C_6H_3$-2,4$Cl_2$ | H |
| $CH_3$ | H | —$C_6H_3$-3,4$Cl_2$ | H |
| | | $R^2 + R^3$ | |
| $CH_3$ | H | =CH—$CH_3$ | |
| $CH_3$ | H | =CH—$C_2H_5$ | |
| $CH_3$ | H | =CH—$C_3H_7$-n | |
| $CH_3$ | H | =CH—$C_3H_7$-iso | |

TABLE 1-continued

| | | |
|---|---|---|
| CH₃ | H | =CH—C₄H₉-n |
| CH₃ | H | =CH—C₄H₉-iso |
| CH₃ | H | =CH—C₄H₉-tert |
| CH₃ | H | =CH—C₅H₁₁-n |
| CH₃ | H | =CH—C₅H₁₁-iso |
| CH₃ | H | =CH—C₆H₁₃-n |
| CH₃ | H | =CH—C₇H₁₅-n |
| CH₃ | H | =CH—C₈H₁₇-n |
| CH₃ | H | =CH—C₉H₁₉-n |
| CH₃ | H | =C(CH₃)₂ |
| CH₃ | H | =C(CH₃)C₂H₅ |
| CH₃ | H | =C(CH₃)C₃H₇-n |
| CH₃ | H | =C(C₂H₅)₂ |
| CH₃ | H | =C(C₃H₇)₂ |
| CH₃ | H | =C(CH₃)C₄H₉-n |
| CH₃ | H | =C(CH₃)C₄H₉-iso |
| CH₃ | H | =C(CH₃)C₄H₉-tert |
| CH₃ | H | =C(CH₃)C₅H₁₁-n |
| CH₃ | H | =C(CH₃)C₆H₁₃-n |
| CH₃ | H | =C(CH₃)C₇H₁₅-n |
| CH₃ | H | =C(CH₃)C₈H₁₇-n |
| CH₃ | H | =C(C₄H₉)C₆H₁₃-n |
| CH₃ | H | =⟨cyclobutylidene⟩ |
| CH₃ | H | =⟨cyclopentylidene⟩ |
| CH₃ | H | =⟨3-methylcyclopentylidene⟩ |
| CH₃ | H | =⟨cyclohexylidene⟩ |
| CH₃ | H | =⟨4-methylcyclohexylidene⟩ |
| CH₃ | H | =⟨3-methylcyclohexylidene⟩ |
| CH₃ | H | =⟨4-tert-butylcyclohexylidene⟩ |
| CH₃ | H | =⟨tetrahydropyran-4-ylidene⟩ |
| CH₃ | H | =⟨tetrahydrothiopyran-4-ylidene⟩ |

TABLE 1-continued

| | | |
|---|---|---|
| CH₃ | H | 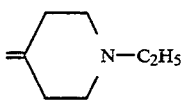 =⟨ ⟩N—CH₃ |
| CH₃ | H | =⟨ ⟩N—C₂H₅ |
| CH₃ | H | =⟨ ⟩N—C₃H₇-n |
| CH₃ | H | =CH—CH=CH₂ |
| CH₃ | H | =CH—CH=CH—CH₃ |
| CH₃ | H | =CH—CH=C(CH₃)₂ |
| CH₃ | H | =CH—C₆H₅ |
| CH₃ | H | =CH—CH₂—C₆H₅ |
| CH₃ | H | =CH—CH₂CH₂—C₆H₅ |
| CH₃ | H | =CH—CH(CH₃)CH₂C₆H₅ |
| CH₃ | H | =CH—CH=CH—C₆H₅ |
| CH₃ | H | =CH—C₆H₄-2F |
| CH₃ | H | =CH—C₆H₄-3F |
| CH₃ | H | =CH—C₆H₄-4F |
| CH₃ | H | =CH—C₆H₄-2Cl |
| CH₃ | H | =CH—C₆H₄-3Cl |
| CH₃ | H | =CH—C₆H₄-4Cl |
| CH₃ | H | =CH—C₆H₃-2OH-5Cl |
| CH₃ | H | =CH—C₆H₃-2OH-3Cl |
| CH₃ | H | =CH—C₆H₂-2OH-3,5Cl₂ |
| CH₃ | H | =CH—C₆H₄-2OH |
| CH₃ | H | =CH—C₆H₄-3OH |
| CH₃ | H | =CH—C₆H₄-4OH |
| CH₃ | H | =CH—C₆H₄-4Br |
| CH₃ | H | =CH—C₆H₃-2OH-3Br |
| CH₃ | H | =CH—C₆H₃-2OH-5Br |
| CH₃ | H | =CH—C₆H₂-2OH-3,5Br₂ |
| CH₃ | H | =CH—C₆HH₃-3Br-4OH |
| CH₃ | H | =CH—C₆H₃-2,4-Cl₂ |
| CH₃ | H | =CH—C₆H₃-3,4-Cl₂ |
| CH₃ | H | =CH—C₆H₄-4CH₃ |
| CH₃ | H | =CH—C₆H₄-4C₃H₇-iso |
| CH₃ | H | =CH—C₆H₄-4C₄H₉-tert |
| CH₃ | H | =CH—C₆H₄-4-C₆H₁₃-n |
| CH₃ | H | =CH—C₆H₄-2OCH₃ |
| CH₃ | H | =CH—C₆H₄-3OCH₃ |
| CH₃ | H | =CH—C₆H₄-4OCH₃ |
| CH₃ | H | =CH—C₆H₃-2,4(OCH₃)₂ |
| CH₃ | H | =CH—C₆H₃-2,5(OCH₃)₂ |
| CH₃ | H | =CH—C₆H₃-3,4(OCH₃)₂ |
| CH₃ | H | =CH—C₆H₃-2,3(OCH₃)₂ |
| CH₃ | H | =CH—C₆H₃-3OH-4OCH₃ |
| CH₃ | H | =CH—C₆H₄-4CF₃ |
| CH₃ | H | =CH—C₆H₄-4NO₂ |
| CH₃ | H | =CH—C₆H₃-2OH-5NO₂ |
| CH₃ | H | =CH—C₆H₄-4-COOC₂H₅ |
| CH₃ | H | =CH—C₆H₄-4-CONH₂ |
| CH₃ | H | =CH—C₆H₄-4-N(CH₃)₂ |
| CH₃ | H | =CH-(thienyl-2) |
| CH₃ | H | =CH-(thienyl-3) |
| CH₃ | H | =CH-(5-chlorothienyl-2) |
| CH₃ | H | =CH-(5-bromothienyl-2) |
| CH₃ | H | =CH-(5-chlorothienyl-3) |
| CH₃ | H | =CH-(5-bromothienyl-3) |
| CH₃ | H | =CH-(5-methylthienyl-2) |
| CH₃ | H | =CH-(5-methylthienyl-3) |
| CH₃ | H | =CH-(furanyl-2) |
| CH₃ | H | =CH-(5-methylfuranyl-2) |
| CH₃ | H | =CH-(pyridinyl-2) |
| CH₃ | H | =CH-(pyridinyl-3) |
| CH₃ | H | =CH-(pyridinyl-4) |
| CH₃ | H | =CH-(isoxazolyl-3) |
| CH₃ | H | =CH-(isoxazolyl-4) |
| CH₃ | H | =CH-(isoxazolyl-5) |
| CH₃ | H | =CH-(5-methylisoxazolyl-3) |
| R² | R³ | |

TABLE 1-continued

| | | | |
|---|---|---|---|
| CH$_3$ | —CH$_2$C$_6$H$_5$ | H | H |
| CH$_3$ | —CH$_2$CH$_2$—C$_6$H$_5$ | H | H |
| CH$_3$ | —(CH$_3$)$_3$—C$_6$H$_5$ | H | H |
| CH$_3$ | —CH$_2$—C$_6$H$_5$-4F | H | H |
| CH$_3$ | —CH$_2$—C$_6$H$_4$-2F | H | H |
| CH$_3$ | —CH$_2$—C$_6$H$_4$-2Cl | H | H |
| CH$_3$ | —CH$_2$—C$_6$H$_4$-4Cl | H | H |
| CH$_3$ | —CH$_2$—C$_6$H$_4$-4CH$_3$ | H | H |
| CH$_3$ | —CH$_2$—C$_6$H$_4$-4OCH$_3$ | H | H |
| CH$_3$ | —CH$_2$C$_6$H$_4$-4C(CH$_3$)$_3$ | H | H |
| CH$_3$ | —CH$_2$C$_6$H$_4$-4OC$_2$H$_5$ | H | H |
| CH$_3$ | —CH$_2$C$_6$H$_4$-4OC$_3$H$_7$ | H | H |
| CH$_3$ | —CH$_2$C$_6$H$_4$-4CF$_3$ | H | H |
| CH$_3$ | —CH$_2$—C$_6$H$_3$-2,4-Cl$_2$ | H | H |
| C$_2$H$_5$ | H | H | H |
| C$_2$H$_5$ | CH$_3$ | H | H |
| C$_2$H$_5$ | CH$_3$ | CH$_3$ | H |
| C$_2$H$_5$ | H | CH$_3$ | CH$_3$ |
| C$_2$H$_5$ | C$_2$H$_5$ | H | H |
| C$_2$H$_5$ | iso-C$_3$H$_7$ | H | H |
| C$_2$H$_5$ | n-C$_3$H$_7$ | H | H |
| C$_2$H$_5$ | H | —C(CH$_3$)$_3$ | H |

| | | R$^2$ + R$^3$ | |
|---|---|---|---|
| C$_2$H$_5$ | H | =CH—C$_4$H$_9$-n | |
| C$_2$H$_5$ | H | =CH—C$_5$H$_{11}$-n | |
| C$_2$H$_5$ | H | =CH—C$_9$H$_{19}$-n | |
| C$_2$H$_5$ | H | =CH—C$_6$H$_5$ | |
| C$_2$H$_5$ | H | =CH—C$_6$H$_4$-2OH | |
| C$_2$H$_5$ | H | =CH—C$_6$H$_3$-2OH-3Cl | |
| C$_2$H$_5$ | H | =CH—C$_6$H$_3$-2OH-5Cl | |

| | | R$^2$ | R$^3$ |
|---|---|---|---|
| C$_2$H$_5$ | H | =CH—C$_6$H$_2$-2OH-3,5Cl$_2$ | |
| C$_2$H$_5$ | H | =CH—C$_6$H$_4$-4Cl | m.p. |
| C$_2$H$_5$ | H | =CH—CH=CH—C$_6$H$_5$ | 330° C. |
| C$_2$H$_5$ | H | =CH—CH=CH—C$_6$H$_4$-4OCH$_3$ | |
| C$_2$H$_5$ | H | cyclopentylidene | |
| C$_2$H$_5$ | H | cyclohexylidene | |
| C$_2$H$_5$ | H | 3-methylcyclohexylidene | |
| C$_2$H$_5$ | H | 4-methylcyclohexylidene | |
| C$_2$H$_5$ | H | C$_6$H$_5$ | H |
| C$_2$H$_5$ | H | C$_6$H$_5$ | CH$_3$ |
| C$_3$H$_7$-n | H | H | H |
| C$_3$H$_7$-n | CH$_3$ | H | H |
| C$_3$H$_7$-n | CH$_3$ | CH$_3$ | H |
| C$_3$H$_7$-n | H | CH$_3$ | CH$_3$ |
| C$_3$H$_7$-n | iso-C$_3$H$_7$ | H | H |
| C$_3$H$_7$-n | H | C$_6$H$_5$ | H |
| C$_3$H$_7$-n | H | C$_6$H$_5$ | CH$_3$ |

| | | R$^2$ + R$^3$ | |
|---|---|---|---|
| C$_3$H$_7$-n | H |  | |

TABLE 1-continued

| | | |
|---|---|---|
| C₃H₇-n | H |  |
| C₃H₇-n | H |  |
| C₃H₇-n | H | 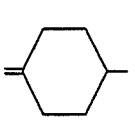 |
| C₃H₇-n | H | 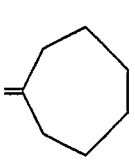 |

| | | R² | R³ |
|---|---|---|---|
| C₃H₇-iso | H | H | H |
| C₃H₇-n | H | =CH—C₉H₁₉-n | |
| C₃H₇-n | H | =CH—C₁₀H₂₁-n | |
| C₃H₇-n | H | =CH—C₁₃H₂₇-n | |
| C₃H₇-n | H | =CH—C₆H₅ | |
| C₃H₇-n | H | =CH—C₆H₄-2OH | |
| C₃H₇-n | H | =CH—C₆H₄-3OH | |
| C₃H₇-n | H | =CH—C₆H₄-4OH | |
| C₃H₇-n | H | =CH—C₆H₃-2OH-3Cl | |
| C₃H₇-n | H | =CH—C₆H₃-2OH-5Cl | |
| C₃H₇-n | H | =CH—C₆H₂-2OH-3,5Cl₂ | |
| C₃H₇-n | H | =CH—C≡CH | |
| C₃H₇-n | H | =CH—C≡C—CH₃ | |

| | | R² | R³ |
|---|---|---|---|
| C₄H₉-n | H | H | H |
| C₄H₉-n | CH₃ | H | H |
| C₄H₉-n | CH₃ | CH₃ | H |
| C₄H₉-n | H | CH₃ | CH₃ |
| C₄H₉-n | iso-C₃H₇ | H | H |
| C₄H₉-n | iso-C₃H₇ | =CH—C₆H₄-2OH | |
| C₄H₉-n | iso-C₃H₇ | =CH—CH=CH—C₆H₄-2OCH₃ | |
| C₄H₉-n | H | —C₆H₅ | H |
| C₄H₉-n | H | —CH₂—C₆H₅ | H |

| | | R² + R³ | |
|---|---|---|---|
| C₄H₉-n | H | =CH—C₁₅H₃₁-n | |
| C₄H₉-n | H | =CH—C₁₇H₃₅-n | |
| C₄H₉-n | H | =CH—C₆H₃-2OH-3Cl | |
| C₄H₉-n | H | =CH—C₆H₃-2OH-5Cl | |
| C₄H₉-n | H |  | |
| C₄H₉-n | H | 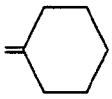 | |
| C₄H₉-n | H | 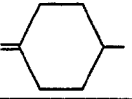 | |

| | | R² | R³ |
|---|---|---|---|
| C₄H₉-iso | H | H | H |
| C₄H₉-iso | CH₃ | H | H |
| C₄H₉-iso | H | CH₃ | H |
| C₄H₉-iso | CH₃ | CH₃ | H |
| C₄H₉-iso | H | CH₃ | CH₃ |

TABLE 1-continued

| | | | |
|---|---|---|---|
| C$_4$H$_9$-iso | C$_2$H$_5$ | H | H |
| C$_4$H$_9$-iso | C$_3$H$_7$-iso | H | H |
| C$_4$H$_9$-iso | H | —C(CH$_3$)$_3$ | H |
| C$_4$H$_9$-iso | H | —C$_6$H$_5$ | H |
| C$_4$H$_9$-iso | H | —C$_6$H$_5$ | CH$_3$ |
| C$_4$H$_9$-iso | H | —C$_6$H$_4$-4F | H |
| C$_4$H$_9$-iso | H | —C$_6$H$_4$-4Cl | H |
| C$_4$H$_9$-iso | H | —C$_6$H$_4$-4CH$_3$ | H |
| C$_4$H$_9$-iso | H | —C$_6$H$_4$-4N(CH$_3$)$_2$ | H |
| C$_4$H$_9$-iso | H | =CH—C$_3$H$_7$-n | |
| C$_4$H$_9$-iso | H | =CH—C$_4$H$_9$-iso | |
| C$_4$H$_9$-iso | H | =CH—C$_5$H$_{11}$-n | |
| C$_4$H$_9$-iso | H | =CH—C$_9$H$_{19}$-n | |
| C$_4$H$_9$-iso | H | =C(CH$_3$)C$_3$H$_7$ | |

| | R$^2$ + R$^3$ | |
|---|---|---|
| C$_4$H$_9$-iso | H | (cyclopentylidene) |
| C$_4$H$_9$-iso | H | (cyclohexylidene) |
| C$_4$H$_9$-iso | H | (4-methylcyclohexylidene) |
| C$_4$H$_9$-iso | H | (4-methylcyclohexylidene, alt) |
| C$_4$H$_9$-iso | H | (4-tert-butylcyclohexylidene) |

| | | |
|---|---|---|
| C$_4$H$_9$-iso | H | =CH—CH=CH—CH$_3$ |
| C$_4$H$_9$-iso | H | =CH—CH=C(CH$_3$)$_2$ |
| C$_4$H$_9$-iso | H | =CH—C$_6$H$_5$ |
| C$_4$H$_9$-iso | H | =CH—CH$_2$—C$_6$H$_5$ |
| C$_4$H$_9$-iso | H | =CH—CH$_2$CH$_2$C$_6$H$_5$ |
| C$_4$H$_9$-iso | H | =CH—CH=CH—C$_6$H$_5$ |
| C$_4$H$_9$-iso | H | =CH—C$_6$H$_4$-4F |
| C$_4$H$_9$-iso | H | =CH—C$_6$H$_4$-4Cl |
| C$_4$H$_9$-iso | H | =CH—C$_6$H$_4$-CF$_3$ |
| C$_4$H$_9$-iso | H | =CH—C$_6$H$_4$-CH$_3$ |
| C$_4$H$_9$-iso | H | =CH—C$_6$H$_4$-4OCH$_3$ |
| C$_4$H$_9$-iso | H | =CH—C$_6$H$_4$-2OH |
| C$_4$H$_9$-iso | H | =CH—C$_6$H$_3$-2OH-3Cl |
| C$_4$H$_9$-iso | H | =CH—C$_6$H$_3$-2OH-5Cl |
| C$_4$H$_9$-iso | H | =CH-(3-pyridinyl) |
| C$_4$H$_9$-iso | H | =CH—CH=CH—C$_6$H$_4$4Cl |

| | R$^2$ | R$^3$ | |
|---|---|---|---|
| C$_4$H$_9$-iso | —CH$_2$—C$_6$H$_5$ | H | H |
| C$_5$H$_{11}$-n | H | H | H |
| C$_4$H$_9$-iso | H | —C$_6$H$_4$-4C(CH$_3$)$_3$ | H |
| C$_4$H$_9$-iso | H | —C$_6$H$_4$-4OCH$_3$ | H |
| C$_4$H$_9$-iso | H | —C$_6$H$_4$-4CF$_3$ | H |
| C$_4$H$_9$-iso | H | —C$_6$H$_4$-4NO$_2$ | H |
| C$_4$H$_9$-iso | —C$_6$H$_4$-4OC$_2$H$_5$ | H | |
| C$_5$H$_{11}$-n | CH$_3$ | H | H |
| C$_5$H$_{11}$-n | CH$_3$ | CH$_3$ | H |
| C$_5$H$_{11}$-n | iso-C$_3$H$_7$ | H | H |
| C$_5$H$_{11}$-n | H | CH$_3$ | CH$_3$ |
| C$_6$H$_{13}$-n | H | H | H |
| C$_6$H$_{13}$-n | CH$_3$ | H | H |
| C$_6$H$_{13}$-n | H | CH$_3$ | CH$_3$ |
| C$_6$H$_{13}$-n | H | C$_6$H$_5$ | H |
| C$_8$H$_{17}$-n | H | H | H |

TABLE 1-continued

| | | | |
|---|---|---|---|
| $C_8H_{17}$-n | $CH_3$ | H | H |
| $C_8H_{17}$-n | iso-$C_3H_7$ | H | H |
| $C_8H_{17}$-n | H | $C_6H_5$ | H |
| $C_{10}H_{21}$-n | H | H | H |
| $C_{10}H_{21}$-n | $CH_3$ | H | H |
| $C_{10}H_{21}$-n | iso-$C_3H_7$ | H | H |
| $C_{10}H_{21}$-n | H | $CH_3$ | $CH_3$ |
| $C_{12}H_{25}$-n | H | H | H |
| $C_{12}H_{25}$-n | $CH_3$ | H | H |
| $C_{12}H_{25}$-n | H | $C_6H_5$ | H |
| $C_{14}H_{29}$-n | H | H | H |
| $C_{14}H_{29}$-n | iso-$C_3H_7$ | H | H |
| $C_{18}H_{37}$-n | H | H | H |
| $C_{20}H_{41}$-n | H | H | H |
| Cl—$CH_2$—$CH_2$— | H | H | H |
| Cl—$(CH_2)_3$— | H | H | H |
| Cl—$(CH_2)_4$— | H | H | H |
| Cl—$(CH_2)_6$— | H | H | H |
| Cl—$(CH_2)_8$— | H | H | H |
| Br—$(CH_2)_4$ | H | H | H |
| $CF_3$—$CH_2$— | H | H | H |
| —$CH_2$—CH=$CH_2$ | H | H | H |
| —$CH_2$—CH=$CH_2$ | H | $CH_3$ | $CH_3$ |
| —$CH_2$—CH=$CH_2$ | iso-$C_3H_7$ | H | H |
| —CH—CH=$CH_2$ | H | $C_6H_5$— | H |
| —$CH_2$—CH=CH—$CH_3$ | H | H | H |
| —$CH_2$—CH=$C(CH_3)_2$ | H | H | H |
| —$CH_2CH_2CH$=$CH_2$ | H | H | H |
| —$CH_2$CH=CH—$C_2H_5$ | H | H | H |
| —$CH_2$CH=CH—$C_3H_7$-n | H | H | H |
| —$CH_2$CH=CH—$C_4H_9$-n | H | H | H |
| —$CH_2$—C(Cl)=$CH_2$ | H | H | H |
| —$CH_2$—CH=CH—CL | H | H | H |
| —$CH_2$—C(Br)=$CH_2$ | H | H | H |
| —$CH_2$—CH=$C(Cl)_2$ | H | H | H |
| $CH_2$—(Cl)=$CCl_2$ | H | H | H |
| —$CH_2$—$CH_2$—$OCH_3$ | H | H | H |
| —$(CH_2)_3OCH_3$ | H | H | H |
| —$(CH_2)_2OC_2H_5$ | H | H | H |
| —$(CH_2)_2OC_3H_7$-n | H | H | H |
| —$(CH_2)_3OC_2H_5$ | H | H | H |
| —$(CH_2)_3OC_3H_7$-n | H | H | H |
| —$(CH_3)_3OC_4H_9$-n | H | H | H |
| —cyclopropyl | H | H | H |
| —cyclobutyl | H | H | H |
| —cyclopentyl | H | H | H |
| —cyclopentylmethyl | H | H | H |
| —cyclohexyl | H | H | H |
| 4-methylcyclohexyl | H | H | H |
| cyclohexylmethyl | H | H | H |
| cycloheptyl | H | H | H |
| —$CH_2$—$C_6H_5$ | H | H | H |
| —$CH_2CH_2C_6H_5$ | H | H | H |
| —$(CH_2)_3C_6H_5$ | H | H | H |
| —$CH_2CH(CH_3)CH_2C_6H_5$ | H | H | H |
| —$CH_2$—CH=CH—$C_6H_5$ | H | H | H |
| —$CH_2$—$C_6H_4$-2F | H | H | H |
| —$CH_2$—$C_6H_4$-4F | H | H | H |
| —$CH_2$—$C_6H_4$-2Cl | H | H | H |
| —$CH_2$—$C_6H_4$-3Cl | H | H | H |
| —$CH_2$—$C_6H_4$-4Cl | H | H | H |
| —$CH_2$—$C_6H_4$-4$CH_3$ | H | H | H |
| —$CH_2$—$C_6H_4$-2$OCH_3$ | H | H | H |
| —$CH_2$—$C_6H_4$-3$OCH_3$ | H | H | H |
| —$CH_2$—$C_6H_4$-4$OCH_3$ | H | H | H |
| —$CH_2$—$C_6H_4$-4$OC_2H_5$ | H | H | H |
| —$CH_2$—$C_6H_4$-4$CF_3$ | H | H | H |
| —$CH_2$—$C_6H_3$-2,4-$Cl_2$ | H | H | H |
| —$(CH_2)_4$—$C_6H_4$—4Cl | H | H | H |

How the novel active ingredients of the formula I are manufactured and used will be apparent from the following examples.

Manufacturing examples

Example 1

1-(Ethoxyamino)-2-(hydrazino)-ethane-1,2-dione

A solution of 234 g (1.59 mol) of methyl (ethoxyamino)-oxoacetate in 450 ml of ethanol was added to a solution of 92.8 g (1.855 mol) of hydrazine hydrate in 300 ml of ethanol and the mixture was stirred for 2 hours at 65° C. The mixture was cooled to +10° C., the precipitate was suction filtered, washed with a small amount of cold ethanol, and dried. There was obtained 150 g (64.2% of theory) of 1-(ethoxyamino)-2-(hydrazino)-ethane-1,2-dione as white crystals of m.p. 182° C.

Example 2

1-(Ethoxyamino)-2-[(4-chlorophenylmethylene)-hydrazino]-ethane-1,2-dione 9 g (0.07 mol) of 4-chlorobenzaldehyde was added to a solution of 10.3 g (0.07 mol) of 1-(ethoxyamino)-2-(hydrazino)-ethane-1,2-dione (Example 1) in 100 ml of acetic acid, and the mixture was stirred for 30 minutes at 40° C. The precipitate was suction filtered, washed with ether and dried. There was obtained 12.2 g (65% of theory) of 1-(ethoxyamino)-2-[4-chlorophenylmethylene)-hydrazino]-ethane-1,2-dione as white crystals of m.p. 330° C. (decomp.).

The compounds of the formula I listed in Table 2 below were obtained analogously to the manufacturing examples and in accordance with the general manufacturing details:

TABLE 2

| No. | R | $R^1$ | $R^2$ | $R^3$ | m.p. (°C.) |
|---|---|---|---|---|---|
| 3 | —$C_2H_5$ | H |  | | 130–131 |
| 4 | —$C_2H_5$ | H |  | | 123–125 |
| 5 | —$C_2H_5$ | H | 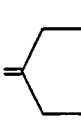 | | 110–112 |
| 6 | —$C_2H_5$ | H | 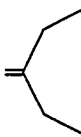 | | 120–122 |
| 7 | —$CH_2$—CH=$CH_2$ | H | H | H | 185–186 |
| 8 | —$CH_2$—CH=$CH_2$ | H | =CH—$C_6H_4$-4Cl | | 300 (decomp.) |
| 9 | —$CH_2$—C(Br)=$CH_2$ | H | H | H | 130–131 |
| 10 | $C_3H_7$-n | H | H | H | 159–161 |
| 11 | $C_3H_7$-n | H | =CH—$C_6H_4$-4Cl | | 258–259 |
| 12 | $C_3H_7$-n | H | =CH—$C_6H_4$-4OCH$_3$ | | 199–201 |
| 13 | $C_3H_7$-n | H | =CH—$C_6H_3$-3,4(OCH$_3$)$_2$ | | 209–211 |
| 14 | $C_3H_7$-iso | H | H | H | 142–145 |
| 15 | $C_3H_7$-iso | H | =CH—$C_6H_4$-4OCH$_3$ | | 243–245 |
| 16 | $C_3H_7$-iso | H | =CH—$C_6H_3$-3,4(OCH$_3$)$_2$ | | 198–201 |
| 17 | $C_3H_7$-iso | H | =CH—$C_6H_2$-3,4,5(OCH$_3$)$_3$ | | 235–238 |
| 18 | $C_3H_7$-iso | H |  | | 158–159 |
| 19 | $C_3H_7$-iso | H |  | | 138–140 |
| 20 | $C_3H_7$-iso | H |  | | 117–118 |
| 21 | $C_3H_7$-iso | H |  | | 120–121 |
| 22 | —$CH_2$—C(CH$_3$)=$CH_2$ | H | H | H | 142–144 |
| 23 | —$CH_2$—C(CH$_3$)=$CH_2$ | H | =CH—$C_6H_4$-4Cl | | 277–280 |
| 24 | —$CH_2$—C(CH$_3$)=$CH_2$ | H | =CH—$C_6H_4$-4CF$_3$ | | 310 (decomp.) |
| 25 | —$CH_2$—C(CH$_3$)=$CH_2$ | H | =CH—$C_6H_4$-4OCH$_3$ | | 300 (decomp.) |
| 26 | —$CH_2$—C(CH$_3$)=$CH_2$ | H | =CH—$C_6H_3$-3,4(OCH$_3$)$_2$ | | 205–208 |
| 27 | $C_4H_9$-n | H | H | H | 150–151 |
| 28 | $C_4H_9$-n | H | =CH—$C_6H_4$-4OCH$_3$ | | 217–220 |

TABLE 2-continued

| No. | R | R$^1$ | R$^2$ | R$^3$ | m.p. (°C.) |
|---|---|---|---|---|---|
| 29 | C$_4$H$_9$-n | H | =CH—C$_6$H$_3$-3,4(OCH$_3$)$_2$ | | 217–219 |
| 30 | C$_4$H$_9$-n | H | =CH—C$_6$H$_3$-3,4Cl$_2$ | | 203–205 |
| 31 | C$_4$H$_9$-iso | H | H | H | 151–153 |
| 32 | C$_4$H$_9$-iso | CH$_3$ | H | H | 130–131 |
| 33 | C$_4$H$_9$-iso | H | CH$_3$ | CH$_3$ | 107–111 |
| 34 | C$_4$H$_9$-iso | C$_3$H$_7$-iso | H | H | 135–136 |
| 35 | C$_4$H$_9$-iso | H | =CH—C$_6$H$_5$ | | 143–146 |
| 36 | C$_4$H$_9$-iso | H | =CH—C$_6$H$_4$-2OH | | 218–220 |
| 37 | C$_4$H$_9$-iso | H | =CH—C$_6$H$_4$-4C(CH$_3$)$_3$ | | 275–277 |
| 38 | C$_4$H$_9$-iso | H | =CH—C$_6$H$_4$-4OCH$_3$ | | 230 |
| 39 | C$_4$H$_9$-iso | H | =CH—C$_6$H$_3$-3,4(OCH$_3$)$_2$ | | 212–215 |
| 40 | C$_4$H$_9$-iso | H | =CH—C$_6$H$_3$-2OH-5Cl | | 238–240 |
| 41 | C$_4$H$_9$-iso | H | =cyclopentylidene | | 153–155 |
| 42 | C$_4$H$_9$-iso | H | =cyclohexylidene | | 122–125 |
| 43 | C$_4$H$_9$-iso | H | =(4-methylcyclohexylidene) | | 112–115 |
| 44 | C$_4$H$_9$-iso | CH$_3$ | =(4-methylcyclohexylidene) | | 157–158 |
| 45 | C$_4$H$_9$-iso | H | =(4-methylcyclohexylidene) | | 105–108 |
| 46 | C$_4$H$_9$-iso | H | =(4-isopropylcyclohexylidene) | | 112–114 |
| 47 | C$_4$H$_9$-iso | H | =cycloheptylidene | | 154–156 |
| 48 | —CH$_2$—C$_6$H$_5$ | H | H | H | 156–158 |
| 49 | —CH$_2$—C$_6$H$_5$ | H | =CH—C$_6$H$_4$-4Cl | | 274–278 |
| 50 | —CH$_2$—C$_6$H$_5$ | H | =CH—C$_6$H$_4$-4OCH$_3$ | | 249–250 |
| 51 | —CH$_2$—C$_6$H$_5$ | H | =CH—C$_6$H$_3$-3,4(OCH$_3$)$_2$ | | 240–241 |
| 52 | C$_2$H$_5$ | H | =(4-tert-butylcyclohexylidene) | | resin |
| 53 | C$_3$H$_7$-iso | H | =(4-tert-butylcyclohexylidene) | | 117–120 |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii.

When the active ingredients are used for treating seed, rates of from 0.001 to 50, and preferably from 0.01 to 10, g of active ingredient per kg of seed are generally required.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of the compound of Example 1 and 10 parts by weight of N-methyl-u-pyrrolidone, which is suitable for application in the form of very fine drops.

II. A mixture of 20 parts by weight of the compound of Example 2, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 3 from Table 2, 40 parts by weight of cyclohexanone, 30 parts by weight of isobutanol, 20 parts by weight of the adduct of 40 moles of ethylene oxide and 1 mole of castor oil. By pouring the mixture into water and finely distributing it therein, and aqueous dispersion is obtained.

IV. An aqueous dispersion of 20 parts by weight of compound no. 4 from Table 2, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the mixture into water and finely distributing it therein, and aqueous dispersion is obtained.

V. A hammer-milled mixture of 80 parts by weight of compound no. 5 from Table 2, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 6 from Table 2 and 97 parts by weight of particulate kaolin. The dust contains 3 wt % of the active ingredient.

VII. An intimate mixture of 30 parts by weight of compound no. 7 from Table 2, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 8 from Table 2, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 9 from Table 2, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The prior art active ingredient used in the following comparative experiments was Tridemorph (A)—disclosed in U.S. Pat. No. 3,686,394.

Use Example 1

Action on Fusarium culmorum in wheat

True leaves of pot-grown wheat seedlings of the "Kanzler" variety were sprayed to runoff with aqueous spray liquors containing (dry basis) 80% of active ingredient and 20% of emulsifier. The next day they were inoculated with a spore suspension of Fusarium culmorum and placed in a climatic chamber of high humidity (>90%) at 22°–24° C. The extent of fungus spread was assessed visually after 6 days.

The results of this experiment show that compounds nos. 9, 10, 14, 27, 31, 35, 41, 45, 46 and 47, when applied as spray liquors containing 500 ppm of active ingredient, have an excellent fungicidal action (10% attack).

Use Example 2

Action on Botrytis cinerea

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

The results of this experiment show that compounds nos. 7, 22, 24, 26, 31, 42, 45 and 46, when applied as spray liquors containing 500 ppm of active ingredient, have a better fungicidal action (10% attack) than prior art active ingredient A (60% attack).

We claim

1. An oxalyl hydrazide-hydroxamic acid derivative of the general formula I

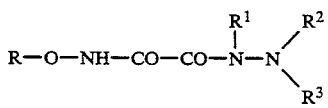

where the substituents have the following meanings:
R, $R^1$, $R^2$ and $R^3$ independently of one another are hydrogen, $C_1$–$C_{20}$-alkyl, $C_3$–$C_{18}$-alkenyl or $C_3$–$C_8$-alkynyl, where these radicals can carry one to five halogen atoms or one to three $C_1$–$C_4$-alkoxy groups, if appropriate together with the halogen atoms;

monocyclic or polycyclic $C_3$–$C_{10}$-cycloalkyl or $C_3$–$C_{10}$-cycloalkylmethyl, where these rings can carry one to three $C_1$–$C_4$-alkyl groups or a cyclohexyl ring;

monocyclic or polycyclic $C_5$–$C_{10}$-cycloalkenyl or $C_5$–$C_{10}$-cycloalkenylmethyl, where these rings can carry one to three $C_1$–$C_4$-alkyl groups or a cyclohexyl ring;

phenyl, phenyl-$C_1$–$C_4$-alkyl, phenyl-$C_2$–$C_6$-alkenyl, where the phenyl radicals can carry one to five halogen atoms or one to three of the following groups, if appropriate together with the halogen atoms: hydroxyl, nitro, $C_1$–$C_4$-alkyl, $C_1$–$C_4$-haloalkyl, $C_1$–$C_4$-alkoxy, $C_1$–$C_4$-haloalkoxy or amines, or $R^2$ together with $R^3$ is the group

where $R^4$ and $R^5$ are one of the radicals R, $R^1$, $R^2$ or $R^3$ or $R^4$, together with $R^5$ and the C atom whose substituents they are, are monocyclic or polycyclic $C_3$–$C_{10}$-cycloalkyl, where these rings can carry one to three $C_1$–$C_4$-alkyl groups or a phenyl ring, wherein R, $R^1$, $R^2$ and $R^3$ are not simultaneously hydrogen.

2. A method for controlling fungi, which comprises treating the fungi or the materials, plants, seeds or the soil threatened by fungal attack with a fungicidally effective amount of an oxalyl hydrazide-hydroxamic acid derivative of the formula of claim 1.

3. A fungicide, containing an inert carrier and a fungicidally effective amount of an oxalyl-hydrazidehydroxamic acid derivative of the formula I of claim 1.

4. A compound of the formula I as claimed in claim 1, where R is ethyl, and $R^1$, $R^2$ and $R^3$ are hydrogen.

5. A compound of the formula I as claimed in claim 1, where R is ethyl, $R^1$ is hydrogen, and $R^2$ and $R^3$ together are the group

wherein $R^4$ and $R^5$ together with the carbon atom to which they are attached are 4-chlorophenylmethylene.

6. A compound of the formula I as claimed in claim 1, where R is ethyl, $R^1$ is hydrogen, and $R^2$ and $R^3$ together are the group

wherein $R^4$ and $R^5$ together with the carbon atom to which they are attached are cyclopentylene.

7. A compound of the formula I as claimed in claim 1, where R is ethyl, $R^1$ is hydrogen, and $R^2$ and $R^3$ together are the group

wherein $R^4$ and $R^5$ together with the carbon atom to which they are attached are cyclohexylene.

8. A compound of the formula I as claimed in claim 1, where R is ethyl, $R^1$ is hydrogen, and $R^2$ and $R^3$ together are the group

wherein $R^4$ and $R^5$ together with the carbon atom to which they are attached are 3-methylcyclohexylene.

9. The acid of claim 1, wherein $R^1$, $R^2$ and $R^3$ independently of one another are hydrogen, $C_1$-$C_{20}$-alkyl, $C_3$-$C_{18}$-alkenyl or $C_3$-$C_8$-alkynyl, where these radicals are unsubstituted or substituted with 1-5 halogen atoms or 1-3 $C_1$-$C_4$ alkoxy groups;

monocyclic or polycyclic $C_3$-$C_{10}$-cycloalkyl or $C_3$-$C_{10}$-cycloalkylmethyl, where these rings are unsubstituted or substituted with 1-3 $C_1$-$C_4$-alkyl groups or a cyclohexyl ring;

monocyclic or polycyclic $C_5$-$C_{10}$-cycloalkenyl or $C_5$-$C_{10}$-cycloalkenylmethyl, where these rings are unsubstituted or substituted with 1-3 $C_1$-$C_4$-alkyl groups or a cyclohexyl ring;

phenyl, phenyl-$C_1$-$C_4$-alkyl, phenyl-$C_2$-$C_6$-alkenyl, where the phenyl ring of these groups is unsubstituted or substituted with 1-5 halogen atoms or 1-3 groups selected from the group consisting of hydroxyl, nitro, $C_1$-$C_4$-alkyl, $C_1$-$C_4$-haloalkyl, $C_1$-$C_4$-alkoxy, $C_1$-$C_4$-haloalkoxy or amines.

10. The acid of claim 9, wherein $R^1$, $R^2$ and $R^3$ independently of one another are hydrogen, $C_1$-$C_{20}$-alkyl, $C_3$-$C_{18}$-alkenyl or $C_3$-$C_8$-alkynyl, where these radicals are unsubstituted or substituted with 1-5 halogen atoms or 1-3 $C_1$-$C_4$ alkoxy groups;

monocyclic or polycyclic $C_3$-$C_{10}$-cycloalkyl or $C_3$-$C_{10}$-cycloalkylmethyl, where these rings are unsubstituted or substituted with 1-3 $C_1$-$C_4$-alkyl groups or a cyclohexyl ring;

monocyclic or polycyclic $C_5$-$C_{10}$-cycloalkenyl or $C_5$-$C_{10}$-cycloalkenylmethyl, where these rings are unsubstituted or substituted with 1-3 $C_1$-$C_4$-alkyl groups or a cyclohexyl ring.

11. The acid of claim 10, wherein $R^1$, $R^2$ and $R^3$ independently of one another are hydrogen, $C_1$-$C_{20}$-alkyl, $C_3$-$C_{18}$-alkenyl or $C_3$-$C_8$-alkynyl, where these radicals are unsubstituted or substituted with 1-5 halogen atoms or 1-3 $C_1$-$C_4$ alkoxy groups.

12. A compound of the formula I as claimed in claim 1, wherein R is isobutyl, $R^1$ is hydrogen, $R^2$ is hydrogen and $R^3$ is hydrogen.

13. An oxalyl hydrazide-hydroxamic acid derivative of the general formula I

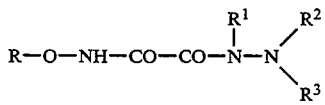

where the substituents have the following meanings:

R is $C_1$-$C_{20}$-alkyl, $C_3$-$C_{18}$-alkenyl or $C_3$-$C_8$-alkynyl, where these radicals can carry one to five halogen atoms or one the three $C_1$-$C_4$-alkoxy groups, if appropriate together with the halogen atoms;

monocyclic or polycyclic $C_3$-$C_{10}$-cycloalkyl or $C_3$-$C_{10}$-cycloalkylmethyl, where these rings can carry one to three $C_1$-$C_4$-alkyl groups or a cyclohexyl ring;

monocyclic or polycyclic $C_5$-$C_{10}$-cycloalkenyl or $C_5$-$C_{10}$-cycloalkenylmethyl, where these rings can carry one to three $C_1$-$C_4$-alkyl groups or a cyclohexyl ring;

phenyl, phenyl-$C_1$-$C_4$-alkyl, phenyl-$C_2$-$C_6$-alkenyl, where the phenyl radicals can carry one to five halogen atoms or one to three of the following groups, if appropriate together with the halogen atoms: hydroxyl, nitro, $C_1$-$C_4$-alkyl, $C_1$-$C_4$-haloalkyl, $C_1$-$C_4$-alkoxy $C_1$-$C_4$-haloalkoxy or amines, $R^1$, $R^2$ and $R^3$ independently of one another are hydrogen, $C_1$-$C_{20}$-alkyl, $C_3$-$C_{18}$-alkenyl or $C_3$-$C_8$-alkynyl, where these radicals can carry one to five halogen atoms or one the three $C_1$-$C_4$-alkoxy groups, if appropriate together with the halogen atoms;

monocyclic or polycyclic $C_3$-$C_{10}$-cycloalkyl or $C_3$-$C_{10}$-cycloalkylmethyl, where these rings can carry one to three $C_1$-$C_4$-alkyl groups or a cyclohexyl ring;

monocyclic or polycyclic $C_5$-$C_{10}$-cycloalkenyl or $C_5$-$C_{10}$-cycloalkenylmethyl, where these rings can carry one to three $C_1$-$C_4$-alkyl groups or a cyclohexyl ring;

phenyl, phenyl-$C_1$-$C_4$-alkyl, phenyl-$C_2$-$C_6$-alkenyl, where the phenyl radicals can carry one to five halogen atoms or one to three of the following groups, if appropriate together with the halogen atoms: hydroxyl, nitro, $C_1$-$C_4$-alkyl, $C_1$-$C_4$-haloalkyl, $C_1$-$C_4$-alkoxy, $C_1$-$C_4$-haloalkoxy or amines, or $R^2$ together with $R^3$ is the group

where $R^4$ and $R^5$ are one of the radicals R, $R^1$, $R^2$, or $R^3$; or $R^4$ together with $R^5$ and the carbon atom whose substituents they are, are monocyclic or polycyclic $C_3$-$C_{10}$-cycloalkyl, where these rings can carry one to three $C_1$-$C_4$-alkyl groups or a phenyl ring.

* * * * *